(12) United States Patent
Wile et al.

(10) Patent No.: US 6,762,391 B2
(45) Date of Patent: Jul. 13, 2004

(54) WELDING ELECTRODE WITH REPLACEABLE TIP

(75) Inventors: Marvin Wile, Cheektowaga, NY (US); David Warchocki, Tonawanda, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 0 days.

(21) Appl. No.: 10/325,027

(22) Filed: Dec. 20, 2002

(65) Prior Publication Data

US 2003/0116539 A1 Jun. 26, 2003

Related U.S. Application Data

(60) Provisional application No. 60/342,294, filed on Dec. 20, 2001.

(51) Int. Cl.[7] .................................................. B23K 11/30
(52) U.S. Cl. ..................................... 219/56.22; 219/119
(58) Field of Search ............................. 219/56.22, 119, 219/120, 56.21

(56) References Cited

U.S. PATENT DOCUMENTS

| | | | |
|---|---|---|---|
| 1,673,020 A | | 6/1928 | Powell |
| 2,068,043 A | | 1/1937 | Warnke |
| 2,795,688 A | | 6/1957 | McCaffrey, Sr. |
| 3,134,883 A | * | 5/1964 | Bennett et al. ............ 219/119 |
| 3,342,972 A | * | 9/1967 | Penberg .................... 219/119 |
| 3,673,681 A | | 7/1972 | Steranko |
| 3,731,046 A | | 5/1973 | Brems |
| 3,794,806 A | | 2/1974 | Klasson |
| 3,838,240 A | | 9/1974 | Schelhorn |
| 3,909,581 A | | 9/1975 | Stone et al. |
| 3,944,777 A | * | 3/1976 | Porat ......................... 219/118 |
| 4,194,107 A | | 3/1980 | Klasson |
| 4,544,822 A | | 10/1985 | Deininger |
| 4,549,065 A | | 10/1985 | Camacho et al. |
| 4,782,210 A | | 11/1988 | Nelson et al. |
| 4,903,884 A | | 2/1990 | Royston et al. |
| 4,910,376 A | | 3/1990 | Riley et al. |
| 5,105,061 A | | 4/1992 | Blankenship |
| 5,122,637 A | | 6/1992 | Bottorff et al. |
| 5,163,600 A | | 11/1992 | Barbarich et al. |
| 5,192,843 A | * | 3/1993 | Cargnel et al. .......... 219/56.22 |
| 5,200,594 A | | 4/1993 | Okada et al. |
| 5,239,162 A | | 8/1993 | Haun et al. |
| 5,296,668 A | | 3/1994 | Foreman et al. |
| 5,332,885 A | | 7/1994 | Landes |
| 5,349,158 A | | 9/1994 | Mari |
| 5,649,355 A | | 7/1997 | Offer |
| 5,734,141 A | | 3/1998 | Voilmy et al. |
| 5,767,472 A | | 6/1998 | Walters |
| 6,011,237 A | | 1/2000 | Yang |

* cited by examiner

Primary Examiner—Clifford C. Shaw
(74) Attorney, Agent, or Firm—Michael F. Scalise

(57) ABSTRACT

A resistance welding electrode that is particularly suited for resistance spot welding a workpiece to a substrate without cross-contaminating specific portions of the workpiece is described. This is done by sheathing an internal surface of the welding electrode with a thermoplastic polymeric material. Then, there is only contact between the welding electrode and the workpiece at the very distal end of the electrode adjacent to where the workpiece is to be connected to the substrate. Contamination in this area is not detrimental because subsequent workpiece plating does not take place there.

20 Claims, 4 Drawing Sheets

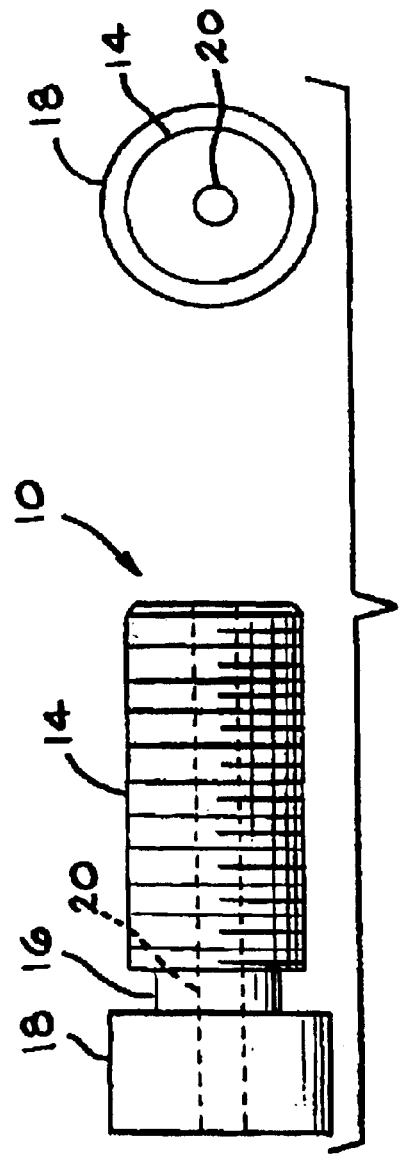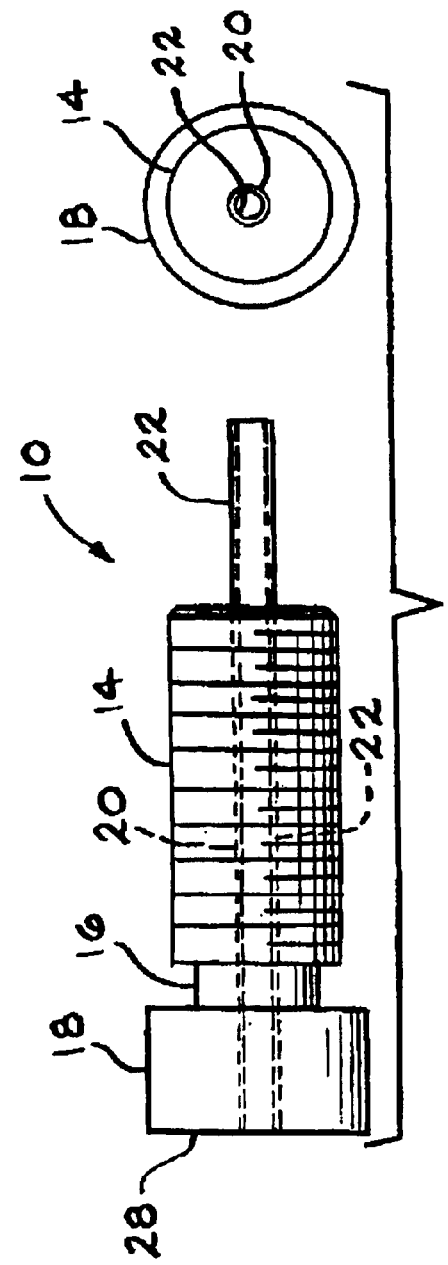

WELDING ELECTRODE WITH REPLACEABLE TIP

CROSS-REFERENCE TO RELATED APPLICATION

This application claims priority based on provisional application Serial No. 60/342,294, filed Dec. 20, 2001.

BACKGROUND OF THE INVENTION

1. Field of the Invention

The present invention relates to electrodes for resistance or elective spot welding, and particularly to construction of such electrodes.

2. Prior Art

In resistance spot welding, it is often difficult to prevent cross contamination of the material of the welding electrode onto the workpiece being welded. In those situations when the welded workpiece is subjected to further processing step, such as plating, cross contamination is undesirable. Often the contamination makes it difficult to plate over the workpiece. An example of this is when a nickel terminal pin is spot welded to the casing of an electrical energy power source for an implantable medical device. Copper is typically used for the welding electrode. However, copper contamination of the nickel surface makes it extremely difficult, if not impossible, to gold plate over the pin. In an implantable power source, the nickel pin welded to the battery or capacitor casing serves as one of the casing terminals. A second terminal pin electrically insulated from the casing by a glass-to-metal seal is the opposite polarity terminal.

What is needed, therefore, is a welding procedure for connecting a workpiece material to a substrate, such as a terminal pin to a casing for an electrical energy power source, that does not result in cross-contamination of the welding electrode material onto the workpiece material.

SUMMARY OF THE INVENTION

The present invention describes a resistance welding electrode that is particularly suited for spot welding a workpiece to a substrate without cross-contaminating specific portions of the workpiece. This is done by sheathing an internal surface of the welding electrode with a thermoplastic polymeric material. Then, there is only contact between the welding electrode and the workpiece at the very distal end of the electrode adjacent to where the workpiece is to be connected to the substrate. Contamination in this area is not detrimental because subsequent workpiece plating does not take place there.

These and other aspects of the present invention will become increasingly more apparent to those skilled in the art by reference to the following description and the appended drawings.

BRIEF DESCRIPTION OF THE DRAWINGS

FIG. 1 is a side elevational view and end view of a tip 10 for a welding electrode 12 according to the present invention.

FIG. 2 is a side elevational view and end view of the welding tip 10 shown in FIG. 1 provided with a polymeric sleeve 22.

DETAILED DESCRIPTION OF THE PREFERRED EMBODIMENTS

Figure 3:
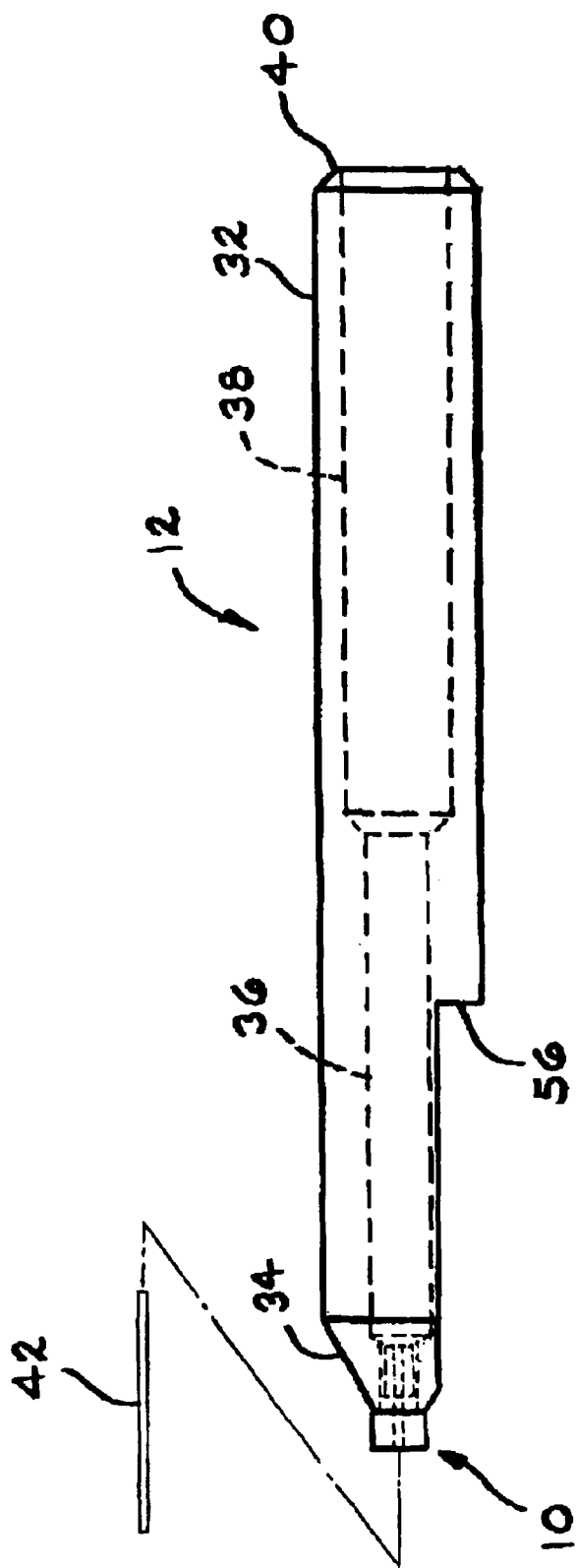
FIG. 3 is a side elevational view of welding electrode 12 including the tip 10 shown in FIG. 2.

Turning now to the drawings, FIGS. 1 and 2 show a tip 10 for a spot welding electrode 12 (FIGS. 3 and 4) according to the present invention. The welding tip 10 is of a conductive material, such as of copper, stainless steel, titanium, aluminum, platinum, tantulum, and alloys thereof having a proximal, threaded section 14 extending to a first cylindrically-shaped section 16 of a reduced diameter. The first cylindrical section 16 steps up to a second cylindrically-shaped section 18 that is not threaded. A cylindrically-shaped bore 20 is provided through the tip 10 centered along its longitudinal axis.

FIG. 2 shows the tip 10 having a relatively thin-walled polymeric sleeve 22 in the shape of tubing received in the bore 20. The sleeve 22 is preferably of a polyimide and of a diameter sufficient to snuggly fit inside the bore 20. An industrial adhesive 24, such as PERMABOND®, secures the sleeve in place. A distal end 26 of the sleeve is provided flush with the distal end wall 28 of the untreaded section 18. However, the sleeve 22 is of a sufficient length to extend beyond the proximal end 30 of the threaded section 14.

Figure 4:
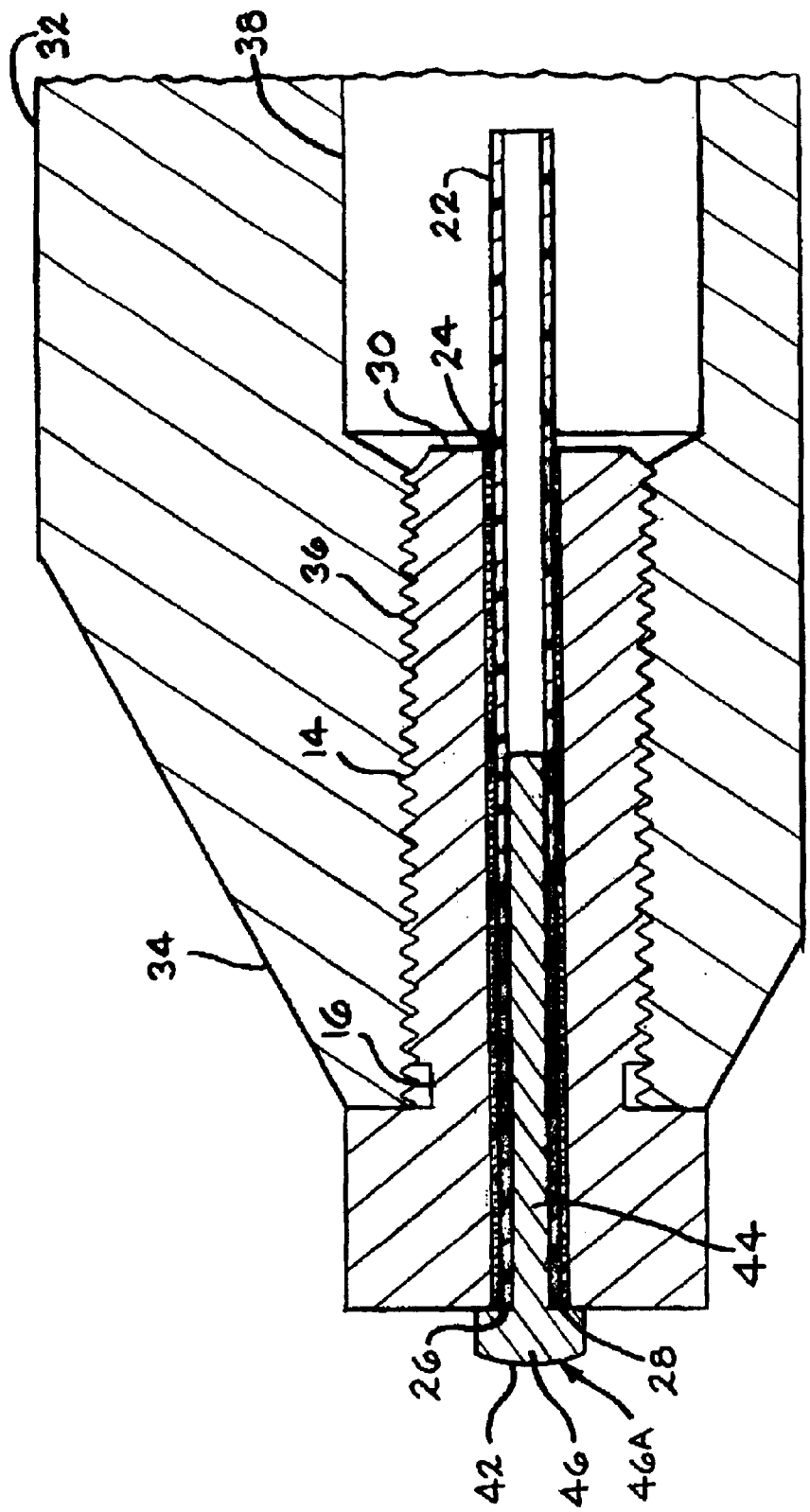
FIG. 4 is an exploded, cross-sectional view of the welding electrode 12 shown in FIG. 3 provided with a workpiece pin 42 that is intended to be spot welded to a substrate.

As shown in FIGS. 3 and 4, the welding tip 10 including the polymeric sleeve 22 is threadingly mated to the welding electrode 12. The electrode comprises a cylindrically-shaped main body 32 having a frusto-conical shaped nose 34. A first, threaded bore 36 is aligned along the longitudinal axis of the electrode 12, extending from the nose 34 and a portion of the distance through the main body 32 where it widens into a second bore 38. The second bore 38 extends to the proximal end 40 of the main body 32 where it is threaded for connection to a welding apparatus (not shown).

In use, a workpiece pin 42 is loaded into the welding tip 10. As shown in FIG. 4, the pin 42 has a cylindrically-shaped shaft portion 44 connected to an enlarged head 46. The shaft 44 is sized to easily move into and out of the polymeric sleeve 22. In the position shown in the figure, the only contact between he welding tip 10 and the pin 42 is at the distal end wall 28 of the tip 10. This is sufficient contact such that when the welding electrode 12 is electrically energized, the distal surface or projection 46A of enlarged head 46 becomes molten. The molten material is then contacted to a substrate support and the electrical current removed from the welding electrode 12. The welding electrode is moved away from the substrate with the polymeric sleeve 22 sliding over the shaft 44 of the pin 42. In this manner, the pin is left behind, welded to the substrate.

Figure 5:
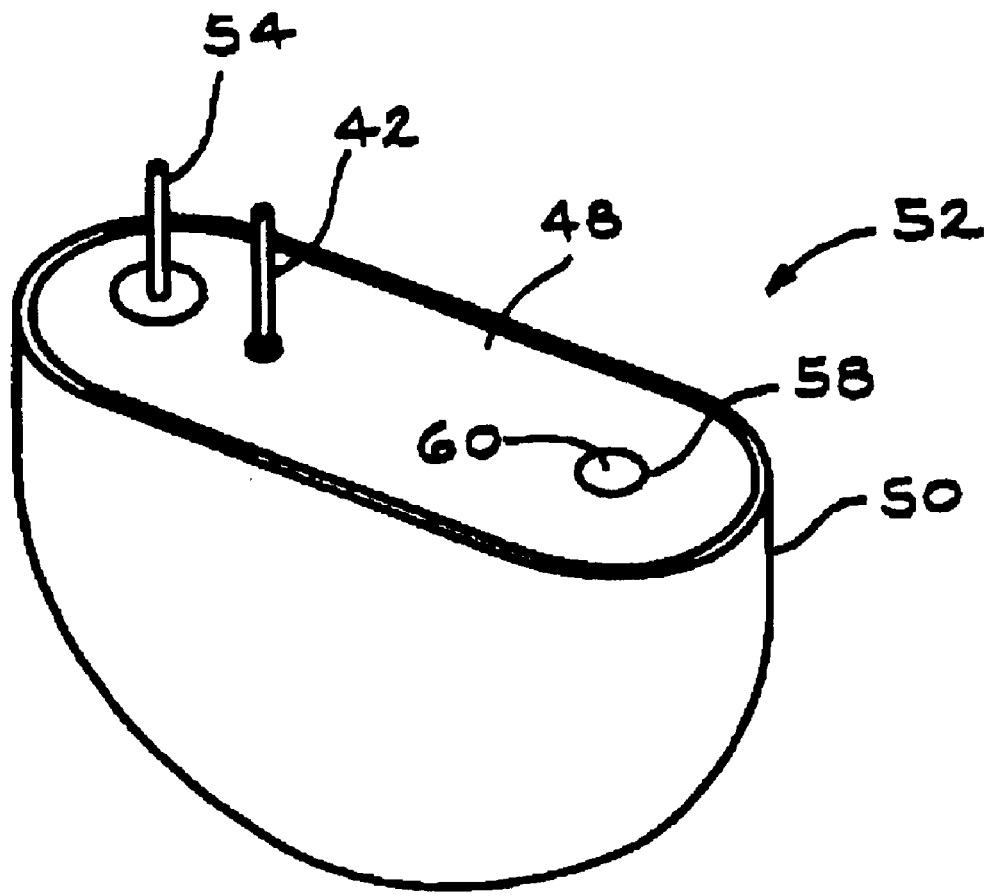
FIG. 5 is a schematic of an electrical energy storage device having the pin 42 welded to its casing to thereby serve as a terminal lead.

FIG. 5 shows the pin 42 after it has been welded to the lid 48 for a casing 50 of an exemplary electrical energy storage device 52. Nickel is a commonly used material for the pin 42. Before the pin is connected to its associated device, however, it is desirable to coat it with a cover material, such as gold. Should copper from the welding electrode contaminate the pin shaft, the gold plating is often of poor quality. The provision of the polymeric sleeve 22 prevents any such cross-contamination. The uncontaminated pin 42 is readily plated along its shaft 44. What little contamination there is at the enlarged head 46 is not a problem because plating does not take place there.

In that respect, the present invention is applicable for use with any type of electrical energy storage device housed inside of a casing. This includes low rate, medium rate, high rate, case negative and case positive electrochemical cells of both primary and secondary chemistries. Examples of such cells include lithium iodine cells, lithium thionychloride cells, lithium silver vanadium oxide cells, lithium carbon monofluoride cells, lithium manganese dioxide cells, and secondary cells containing lithium cobalt oxide, and the like.

In any event, these types of electrical energy storage devices are typically constructed with the casing serving as the terminal for one of the electrodes, such as the negative electrode, and a terminal lead 54 connected to the other electrode, such as the positive electrode. This is referred to as a case negative design. In that respect, the pin 42 directly connected to the casing 50 provides a structure for connecting to a device to be powered by the electrical energy storage device.

As shown in FIG. 3, the welding electrode 12 is provided with a cut-out portion 56. The cut-out 56 is so that the electrode 12 does not contact the therminal lead 54 as the pin 42 is being welded to the lid 48. The electrical energy storage device is complete by a fill opening 58 sealed with a closure member, such as a metal ball 60. The opening 58 is for filling an electrolyte into the casing for activating the negative and positive electrodes.

It will further be recognized that such electrical energy storage devices may take one of various configurations. For example, depending on the type the configuration of the anode, cathode, terminal lead, and fill opening, etc. will vary. Also, when the electrical energy storage device is an electrochemical cell, the materials housed inside the casing will vary. Such materials may take the form of a liquid or a solid depending on the type of cell. Therefore, it should be clear that the present invention is in no manner limited to a specific type of electrochemical chemistry.

The present invention is also applicable to connecting pins to capacitors, such as those described in U.S. Pat. Nos. 5,926,362 and 6,334,879, both to Muffoletto et al. These patents are assigned to the assignee of the present invention and incorporated herein by reference.

It is appreciated that various modifications to the inventive concepts described herein may be apparent to those of ordinary skill in the art without departing from the spirit and scope of the present invention as defined by the appended claims.

What is claimed is:

1. A welding apparatus, which comprises:
   a) a welding electrode;
   b) a tip connected to the electrode, wherein the tip has a tip bore extending to a distal tip end; and
   c) a polymeric sleeve housed inside the tip bore in a snug fitting relationship, wherein the sleeve has a sleeve bore sized to slidingly receive a workpiece therein such that the sleeve contacts the workpiece and prevents the workpiece from contacting the tip except at the distal tip end.

2. The welding apparatus of claim 1 wherein the tip bore extends along the longitudinal axis of the tip.

3. The welding apparatus of claim 1 wherein the polymeric sleeve is of a cylindrical shape.

4. The welding apparatus of claim 1 wherein the polymeric sleeve is of a polyimide.

5. The welding apparatus of claim 1 wherein a distal end of the polymeric sleeve is substantially flush with the distal tip end.

6. The welding apparatus of claim 1 wherein the tip is threadingly mated to the welding electrode.

7. A tip for a welding electrode, the tip comprising:
   a) a proximal section adapted for connection to a welding electrode;
   b) a distal section extending to a distal tip end;
   c) a tip bore extending through at least the distal section of the tip to the distal tip end; and
   d) a polymeric sleeve housed in the tip bore in a snug fitting relationship, wherein the sleeve has a sleeve bore sized to slidingly receive a workpiece therein such that the sleeve contacts the workpiece and prevents the workpiece from contacting the tip except at the distal tip end.

8. The tip of claim 7 wherein the tip bore is aligned along the longitudinal axis of the tip.

9. The tip of claim 7 wherein the polymeric sleeve is of a cylindrical shape.

10. The tip of claim 7 wherein the polymeric sleeve is of a polyimide.

11. The tip of claim 7 wherein a distal end of the polymeric sleeve is substantially flush with the distal tip end.

12. The tip of claim 7 wherein the tip is threadingly mated to the welding electrode.

13. A method for connecting a workpiece to a substrate, comprising the steps of:
   a) providing a welding apparatus comprising:
      i) a welding electrode;
      ii) a tip connected to the electrode, wherein the tip is a bore; and
      iii) a polymeric sleeve housed inside the bore of the tip;
   b) moving the workpiece into the bore of the tip such that a first distal end of the workpiece in contact with a second distal end of the tip with the polymeric sleeve disposal intermediate at least some portion of the workpiece received within the bore;
   c) moving the welding apparatus such that the first distal end of the workpiece contacts a substrate;
   d) electrically energizing the welding apparatus to cause at least a portion of the first distal end of the workpiece to become molten; and
   e) moving the welding apparatus away from the workpiece welded to the substrate.

14. The method of claim 13 including providing the bore extending along the longitudinal axis of the tip.

15. The method of claim 13 including providing the polymeric sleeve of a cylindrical shape.

16. The method of claim 13 including providing the polymeric sleeve of a polyimide.

17. The method of claim 13 including providing a distal end of the polymeric sleeve being substantially flush with a distal end of the tip.

18. The method of claim 13 including providing the tip being threadingly mated to the welding electrode.

19. The method of claim 13 including providing the substrate as an external surface of an electrical energy storage device.

20. The method of claim 13 including selecting the worpiece from the group consisting of copper, stainless steel, titanium, aluminum, platinum, tantulum, and alloys thereof.

* * * * *